United States Patent
Robichon

(10) Patent No.: US 7,588,909 B2
(45) Date of Patent: Sep. 15, 2009

(54) **METHOD FOR DETECTING *STREPTOCOCCUS AGALACTIAE* USING α-GLUCOSIDASE ACTIVITY**

(75) Inventor: Denis Robichon, Blyes (FR)

(73) Assignee: Biomerieux, Marcy l'Etoile (FR)

( * ) Notice: Subject to any disclaimer, the term of this patent is extended or adjusted under 35 U.S.C. 154(b) by 208 days.

(21) Appl. No.: 11/660,867

(22) PCT Filed: Sep. 14, 2005

(86) PCT No.: PCT/FR2005/050740

§ 371 (c)(1), (2), (4) Date: Feb. 22, 2007

(87) PCT Pub. No.: WO2006/032810

PCT Pub. Date: Mar. 30, 2006

(65) Prior Publication Data

US 2007/0292908 A1 Dec. 20, 2007

(30) Foreign Application Priority Data

Sep. 16, 2004 (FR) .................................. 04 52066

(51) Int. Cl.
*C12Q 1/34* (2006.01)
*C12Q 1/14* (2006.01)

(52) U.S. Cl. .......................................... 435/18; 435/36

(58) Field of Classification Search ........................ None
See application file for complete search history.

(56) References Cited

U.S. PATENT DOCUMENTS

| | | | |
|---|---|---|---|
| 5,888,760 A | 3/1999 | Godsey et al. | |
| 6,105,632 A | 8/2000 | Buhlmann | |
| 6,130,057 A * | 10/2000 | Gosnell et al. | 435/32 |
| 2002/0147317 A1 | 10/2002 | Bentsen et al. | |
| 2006/0257967 A1* | 11/2006 | Restaino | 435/34 |

FOREIGN PATENT DOCUMENTS

| | | |
|---|---|---|
| EP | 0 656 421 A1 | 6/1995 |
| JP | A-45-007009 | 4/1970 |
| JP | A-2001-503648 | 3/2001 |
| WO | WO 97/44093 | 11/1997 |
| WO | WO 99/09207 A1 | 2/1999 |
| WO | WO 01/30794 A1 | 5/2001 |

OTHER PUBLICATIONS

Davis et al. Polysaccharase Activity in *Streptococcus agalactaie* (Group B Streptococci); Journal of General Microbiology, vol. 128 (1982) pp. 1381-1384.*
Cheung et al. Stability of Amphotericin B in Fungal Culture Media; Antimicrobial Agents and Chemotherapy, vol. 8, No. 4 (1975) pp. 426-428.*
Wood et al. Aztreonam Selective Agar for Gram Positive Bacteria; Journal of Clinical Pathology, vol. 46 (1993) pp. 769-771.*
Rosa-Fraile et al. Pigment Production by *Streptococcus agalactiae* in Quasi-Defined Media; vol. 67, No. 1 (2001) pp. 473-474.*
Kegg Enzymes-*Streptococcus pneumoniae* G54 downloaded from http://www.genome.jp/kegg-bin/get_htext?htext=spx01000.keg&query=SPG_2086&filedir=/kegg/brite/spx&option=-a; on Dec. 31, 2008.*
Rice et al., "A rapid biochemical test to aid identification of *Mycoplasma mycoides* subsp. *mycoides* small colony (SC) strains," *Letters in Applied Microbiology*, vol. 30, pp. 70-74 (2000).
Schrag, S., et al. "Prevention of Perinatal Group B Streptococcal Disease: Revised Guidelines from CDC," *Morbidity and Mortality Weekly Report*, vol. 51, No. RR-11, pp. 1-23, Aug. 16, 2002.
Glycosynth: Indolyl [Indoxyl] Substrates, pp. 1 & 2, retrieved on Jun. 11, 2007 from: URL:http://www.glycosynth.co.uk/pages/9.htm.
Biosynth: Biochemica & Synthetica, pp. 31, 36, 41 and 46, retrieved from: URL:http://www.biosynth.com (page last updated on Apr. 3, 2006).
Rice; Letters in Applied Microbiology; 2000; vol. 30, pp. 70-74.

* cited by examiner

*Primary Examiner*—Rebecca E. Prouty
*Assistant Examiner*—Paul C. Martin
(74) *Attorney, Agent, or Firm*—Oliff & Berridge, PLC

(57) ABSTRACT

The present invention concerns a method for specifically detecting and identifying *Streptococcus agalactiae,* using a reaction medium comprising at least one α-glucosidase enzymatic substrate.

9 Claims, No Drawings

METHOD FOR DETECTING STREPTOCOCCUS AGALACTIAE USING α-GLUCOSIDASE ACTIVITY

The present invention relates to the field of the detection and identification of *Streptococcus agalactiae*. More particularly, the invention relates to the use of α-glucosidase enzymatic substrates for detecting and identifying *Streptococcus agalactiae*.

The *Streptococcus* genus contains numerous species of a very wide spread in streptococci nature, on the skin of the mucous membranes of humans and animals, and are responsible for multiple infections. They are ubiquitous bacteria that are found in the free state in the outside environment (soil, air, water), in the saprophyte state or in the commensal state in humans and animals. They are located in the rhinopharynx for group A, C, G and H streptococci and *salivarius*, the intestine for group D fetal streptococci and the vaginal cavity for group B streptococci. Their pathogenic role is extremely varied and depends on the species in question and on their location in the organism.

Streptococci are Gram+cocci, 0.5 to 1 µm in diameter, they exhibit grouping in the form of a small chain and are immobile. They are catalase-negative, have a fermentative metabolism, and they are optionally anaerobic and are sensitive to variations in temperature (optimal growth 37° C.) and to variations in pH (optimal pH 7).

*Streptococcus agalactiae* (or *streptococcus* B) is recognized as one of the main infectious agents responsible for mastitis in cattle. In humans, it is essentially a saprophyte of the female genital tract (vagina), but it is also found in the rhinopharynx and in the intestine, in particular the rectum. In adults, colonization often remains asymptomatic, but *Streptococcus agalactiae* can be responsible for septicemia, pneumonia, meningitis, arthritis, urinary infections and deep suppurations. In women who are pregnant, or after having given birth, the infection may lead to endometritis and to sterility.

In newborns, the contamination occurs in utero or, most commonly, during birth, due to inhalation of the amniotic fluid or of vaginal secretions. An early infection often appears immediately after birth or within the first hours of life. Early infection is promoted by premature birth, rupture of the membranes and a strong colonization of the mother's vagina. The mortality rate in this type of infection is very high (>50%). Late infections are generally reflected by meningitis (infantile meningitis) and arthritis.

Systematic screening for the carrying of *Streptococcus agalactiae* is recommended at the end of pregnancy, ideally between 34 and 38 weeks of amenorrhea (35-37 weeks of pregnancy), due in particular to its prevalence (10% in France, i.e. at least 75 000 pregnant women/year) and to the consequences thereof during full-term births, which makes it a public health problem.

Selective media and/or media which make it possible to direct the diagnosis are commercially available. However, these media have the drawback that they are not sufficient on their own for the diagnosis of *Streptococcus agalactiae* and that it is necessary to carry out supplementary tests, such as demonstrating the presence group B Lancefield antigen (polysaccharide with dominant presence of rhamnose) and hippurate hydrolysis (hippurate broth).

The selective media most commonly used are Todd-Hewitt broth, an enrichment broth for searching for group B streptococci in pregnant women. This broth contains various antibiotics that inhibit most gram-negative microorganisms of the accompanying flora, such as nalixidic acid and gentamycin, or nalixidic acid, polymyxin and crystal violet.

After the enrichment step, the antibiotic-supplemented Todd-Hewitt broth must be subcultured on media for searching for streptococci (see CDC (Center for Disease Control) recommendations, MMWR (Morbidity and Mortality Weekly Report), Aug. 16, 2002, Vol. 51, No. RR-11).

Lim medium is a variant of Todd-Hewitt broth and it contains 1% of yeast extract, nalixidic acid and colistin.

A Columbia agar containing 5% of blood is also used and makes it possible in particular, to demonstrate the β-hemolytic characteristic of *Streptococcus agalactiae*. However, this characteristic is not always apparent: the hemolytic halo around the colonies may be narrow, giving rather the α-hemolytic, or even γ-hemolytic, appearance. On the other hand, this characteristic becomes clear if, in the area of the *Streptococcus agalactiae* colonies, there are *Staphylococcus aureus* colonies (Camp-factor).

The drawbacks of these selective media are that they must be supplemented with biochemical tests and/or immunoassays.

Currently, the only commercially available, ready-to-use selective medium that makes it possible to directly isolate and identify *Streptococcus agalactiae* from rectovaginal samples is Granada medium (Biolys SA). This medium has the characteristic of promoting the production of a carotenoid pigment by *Streptococcus agalactiae* strains due to the presence in the medium of soluble starch, proteose peptone No. 3, glucose, sodium pyruvate, magnesium sulfate, methotrexate, colistin, crystal violet, agar, horse serum, anhydrous $Na_2HPO_4$, metronidazole, MOPS (morpholinopropane-sulfonic acid) hemi-sodium salt and distilled water, and incubation under anaerobic conditions. This medium therefore has the drawback that the direct detection of *Streptococcus agalactiae* is carried out under anaerobic conditions, which is not easy to implement. Moreover, no detection medium containing one or more enzymatic substrates is available.

The applicant has demonstrated, against all expectations, that it is possible to use enzymatic substrates, in particular α-glucosidase enzymatic substrates, for specifically detecting and identifying *Streptococcus agalactiae*.

Specifically, surprisingly, not only are the enzymatic substrates used by the *Streptococcus agalactiae*, allowing them to be revealed, for example by producing a modification of the coloration of the colonies in the medium when a chromogenic enzymatic substrate is used, with no diffusion of the coloration in the reaction medium and said coloration therefore remaining concentrated at the colonies, but these molecules have no harmful effect on the growth of these bacteria.

Thus, a subject of the present invention is a method for specifically detecting and identifying *Streptococcus agalactiae*, characterized in that a reaction medium comprising at least one α-glucosidase enzymatic substrate is used.

The α-glucosidase enzymatic substrates suitable for the purposes of the invention are any substrate known to those skilled in the art that makes it possible to demonstrate such an enzymatic activity. Such substrates may, for example, be chromogenic or fluorescent and are described, for example, in the article by P. Rice et al. (2000). A rapid biochemical test to aid identification of *Mycoplasma mycoides* subsp. *mycoides* small colony (SC) strains. Lett. Appl. Microbiol. 1:70-74, or in the BIOSYNTH catalogue, Substrates and Reagents or in the GLYCOSYNTH catalogue, enzyme substrates catalouge.

By way of example, mention may be made of indoxyl-derivative-based substrates, umbelliferone-derivative-based substrates and naphthol-derivative-based substrates.

According to a preferred embodiment of the invention, the enzymatic substrate suitable for the purposes of the invention is an indoxyl-derivative-based substrate.

Examples of such indoxyl derivatives include 3-indolyl-α-D-glucopyranoside derivatives, preferably halogenated derivatives of these compounds.

By way of examples of halogenated 3-indolyl-α-D-glucopyranoside derivatives, mention may be made of 6-bromo-3-indolyl-α-D-glucopyranoside, 6-chloro-3-indolyl-α-D-glucopyranoside, 5-bromo-6-chloro-3-indolyl-α-D-glucopyranoside, 5-bromo-4-chloro-3-indolyl-α-D-glucopyranoside and 5-bromo-4-chloro-3-indolyl-N-methyl-α-D-glucopyranoside, the latter compound being particularly preferred.

The reaction medium as used in the method of the invention is therefore a detection reaction medium due to the presence of the enzymatic substrate.

This reaction medium can be used either as a visualization medium only, or as a culture and visualization medium. In the first case, the culturing of the microorganisms is carried out before inoculation and, in the second case, the reaction medium also constitutes the culture medium.

The reaction medium may be solid, semi-solid or liquid. The term "solid or semi-solid medium" is intended to mean, for example, a gelled medium.

Agar is the conventional solid medium in microbiology for culturing microorganisms, but it is possible to use gelatin or agarose. A certain number of preparations are commercially available, for instance Columbia agar, Trypcase-soy agar, MacConkey agar, Sabouraud agar or, more generally, those described in the Handbook of Microbiological Media (CRC Press).

The amount of agar in the reaction medium is from 2 to 40 g/l. For the solid media, the amount of agar is preferably from 9 to 25 g/l, more preferably from 12 to 14 g/l. For the semi-solid media, the amount of agar is preferably from 2 to 6 g/l.

The enzymatic substrates of the invention can be used in a wide pH range, in particular between pH 5.5 and 10.

The concentration of the enzymatic substrate in the reaction medium is between 10 and 2000 mg/l, preferably between 50 and 500 mg/l, more preferably between 100 and 400 mg/l, which constitutes a preferred embodiment of the invention.

Of course, those skilled in the art would determine the concentration of the enzymatic substrate in the medium within this range, according to the substrate chosen. Thus, insofar as the enzymatic substrate used is 5-bromo-4-chloro-3-indolyl-N-methyl-α-D-glucopyranoside, a concentration between 130 and 300 mg/l is preferred.

The reaction medium that can be used for the purposes of the invention may also comprise other components of use for improving the specificity and the sensitivity of the method of the invention.

The reaction medium may also contain a mixture of inhibitors for inhibiting or limiting the growth of unwanted strains, such as false-positive strains, for example *Candida* or *Staphylococcus saprophyticus*, without modifying the detection sensitivity of the medium.

In this respect, the reaction mixture may contain a mixture of antibiotics. The addition of antibiotics to the reaction medium allows, inter alia, a gain in time since the identification of *Streptococcus agalactiae* is carried out directly.

Examples of antibiotics that are suitable for the purposes of the invention include aztreonam and amphotericin B. These antibiotics are commercially available from ICN, Squibb or Sigma.

Thus, according to one embodiment of the invention, the reaction medium used in the method for specifically detecting and identifying *Streptococcus agalactiae* also comprises a mixture of aztreonam and amphotericin B.

The amount of each antibiotic in the reaction medium varies according to the antibiotic concerned, and will be readily determined by those skilled in the art.

Thus, for example, the concentration of aztreonam may be between 0.01 and 0.08 g/l and the concentration of amphotericin B may be between 0.002 and 0.006 g/l.

A preferred mixture of these antibiotics contains 0.064 g/l of aztreonam and 0.004 g/l of amphotericin B.

The reaction medium used in the method of the invention may also comprise at least one other substrate specific for an enzymatic activity other than that detected by the α-glucosidase substrate. The enzymatic hydrolysis of the other substrate(s) generates a detectable signal different than the signal detected by means of the α-glucosidase substrate, such as, for example, different colored or fluorescent products, so as to allow the demonstration, such as the detection and/or the identification and/or the quantification, of *Streptococcus agalactiae* by improving the specificity of demonstration.

By way of another specific substrate, mention may be made of β-cellobiosidase substrates, β-glucosidase substrates, β-glucosaminidase substrates and any other enzymatic substrate known to those skilled in the art that makes it possible to eliminate false positives.

According to a preferred embodiment, the reaction medium also comprises at least one other substrate for different enzymatic activity, preferably chosen from β-cellobiosidase substrates and β-glucosaminidase substrates.

The use of a β-cellobiosidase substrate such as 6-chloro-3-indolyl-β-D-cellobioside makes it possible to eliminate false-positive species, such as *Enteroccocus faecalis, Listeria monocytogenes* and *Enterobacter claocae*, without degrading the sensitivity of detection of the α-glucosidase activity of *Streptococcus agalactiae*.

The use of a glucosaminidase substrate such as 6-chloro-3-indolyl-β-N-acetylglucosaminide or 5-bromo-6-chloro-3-indolyl-β-N-acetylglucosaminide makes it possible to eliminate the detection of *Enteroccocus faecalis, Enteroccocus faecium* and *Enterobacter claocae*.

The concentration of the other specific enzymatic substrate is generally between 0.01 and 2 g/l. Those skilled in the art will be able to readily determine such a concentration according to the substrate used.

When 6-chloro-3-indolyl-β-D-cellobioside or 6-chloro-3-indolyl-β-N-acetylglucosaminide is used, its concentration in the medium is preferably 0.4 g/l.

The reaction medium may also comprise one or more elements in combination, such as amino acids, peptones, carbohydrates, nucleotides, minerals, vitamins, surfactants, buffers, phosphate salts, ammonium salts, sodium salts or metal salts. Examples of media are described in the applicant's patent applications EP 656 421 and WO99/09 207.

The implementation of the method of the invention can be carried out according to the following steps consisting in:
a) inoculating a reaction medium as defined above, with all or part of the sample,
b) incubating the inoculated medium,
c) revealing the presence of at least one α-glucosidase activity alone or in combination with at least one other enzymatic activity other than an α-glucosidase activity, which constitutes another subject of the invention.

The inoculation and incubation steps are widely known to those skilled in the art.

For example, the incubation temperature may be 37° C. As regards the incubation atmosphere, it is preferably aerobic.

The revealing is carried out with the naked eye by visualization of a change in coloration that does not diffuse in the reaction medium and is therefore concentrated at the colonies. In the case of the revelation of fluorescence, the fluorescence-reading devices known to those skilled in the art are used.

The biological samples to be analyzed are any clinical sample liable to contain *Streptococcus agalactiae*, such as a vaginal specimen, a urine specimen or any other sample of which the analysis may aid a clinician in reaching a diagnosis.

The invention will be understood more clearly from the following examples given by way of nonlimiting illustration.

EXAMPLE 1

Detection of *Streptococcus agalactiae* using α-glucosidase Enzymatic Substrates 1.1 Preparation of the Reaction Media The reaction media were prepared by mixing heart-brain extract (4.84 g/l; Solabia), meat infusion (1.96 g/l; Solabia), biothione (1 g/l; Solabia), biotrypcase (7.2 g/l; Solabia), sodium carbonate (0.3 g/l; VWR), sodium pyruvate (2 g/l; Fluka), HEPES buffer (0.4 g/l; Sigma), lactalbumin peptone (2 g/l; DMV), glucose (1 g/l; Merck), American agar (2 g/l; Sobigel) and European agar (12 g/l; Roko).

After autoclaving for 15 min at 121° C., an α-glucosidase enzymatic substrate as indicated below is added at a rate of 0.1 g/l, followed by cooling in a water bath at 50° C.

6-bromo-3-indolyl-α-D-glucopyranoside (RedA-α-Glu; Inalco), 6-chloro-3-indolyl-α-D-glucopyranoside (Rose-α-Glu; Inalco), 5-bromo-6-chloro-3-indolyl-α-D-glucopyranoside(Magenta-α-Glu; Glycosynth), 5-bromo-4-chloro-3-indolyl-α-D-glucopyranoside (X-α-Glu; Biosynth) and 5-bromo-4-chloro-3-indolyl-N-methyl-α-D-glucopyranoside (GreenA-α-Glu; Inalco).

The media were then poured into a Petri dish for subsequent inoculation with bacterial strains.

1.2 Inoculation of the Microorganism Strains

Eight *Streptococcus agalactiae* strains derived from the applicant's collection, suspended in physiological saline, were inoculated so as to give isolated colonies on each of the media. The dishes were then incubated at 37° C. for 48 hours. The colonies formed are examined visually after 18, 24 and more than 40 hours of incubation. The coloration of these colonies, the growth and also the intensity of this coloration were noted.

1.3 Results

The results are given in table 1 below and are expressed:

in terms of growth (G) with the size being indicated in mm, in terms of intensity (I) of coloration based on an arbitrary scale ranging from 0 to 4, 0 corresponding to an absence of activity and 4 corresponding to the presence of a very intense coloration, in terms of color (Co) with T=turquoise, R=pink or red, Gr=green, Mg=magenta, according to the incubation time in hours (T).

The results as indicated in table 1 demonstrate that streptococci B can be detected using an α-glucosidase enzymatic substrate, at least from 18 h of incubation.

| Strains (accession No.) | T | Medium 1 X-alpha-Glu | | | Medium 2 RedA-alpha-Glu | | | Medium 3 GreenA-alpha-Glu | | | Medium 4 Rose-alpha-Glu | | | Medium 5 Magenta-alpha-Glu | | |
|---|---|---|---|---|---|---|---|---|---|---|---|---|---|---|---|---|
| | | G | I | Co | G | I | Co | G | I | Co | G | I | Co | G | I | Co |
| *Streptococcus agalactiae* (7611003) | 18 | 1 | 2.3 | T | 1 | 0.5 | R | 1 | 2 | Gr | 1 | 0.3 | R | 0.5 | 1 | Mg |
| | 24 | 1.2 | 2.7 | T | 1 | 0.8 | R | 1.3 | 2 | Gr | 1.3 | 0.6 | R | 0.7 | 2 | Mg |
| | >40 | 1.5 | 3 | T | 1.3 | 2 | R | 1.7 | 3 | Gr | 1.7 | 1.3 | R | 0.7 | 3 | Mg |
| *Streptococcus agalactiae* (7701031) | 18 | 0.5 | | | 0.5 | | | 0.5 | | | 0.5 | | | 0.5 | | |
| | 24 | 0.7 | | | 0.7 | | | 0.7 | 0.3 | Gr | 0.7 | | | 0.5 | | |
| | >40 | 1.2 | | | 1.2 | 0.5 | R | 1.5 | 0.8 | Gr | 1.2 | 0.5 | R | 0.8 | 2 | Mg |
| *Streptococcus agalactiae* (7702055) | 18 | 0.7 | 0.5 | T | 0.7 | | | 0.7 | 1 | Gr | 0.7 | 0.1 | R | 0.5 | 0.5 | Mg |
| | 24 | 1 | 1 | T | 1 | 0.3 | R | 0.8 | 2 | Gr | 1 | 0.1 | R | 0.8 | 0.6 | Mg |
| | >40 | 1.7 | 3 | T | 1.7 | 2.3 | R | 1.7 | 3 | Gr | 1.7 | 1 | R | 1 | 3 | Mg |
| *Streptococcus agalactiae* (8709013) | 18 | 0.4 | 0.1 | T | 0.5 | | | 0.4 | 0.5 | Gr | 0.4 | | | 0.4 | 0.5 | Mg |
| | 24 | 0.5 | 0.6 | T | 0.5 | | | 0.5 | 1 | Gr | 0.5 | | | 0.5 | 1.3 | Mg |
| | >40 | 0.7 | 2 | T | 0.7 | 0.8 | R | 0.7 | 2.7 | Gr | 0.7 | 0.5 | R | 0.7 | 2.7 | Mg |
| *Streptococcus agalactiae* (8904053) | 18 | 0.7 | 0.3 | T | 0.7 | | | 0.7 | 0.5 | Gr | 0.7 | 0.1 | R | 0.7 | 0.6 | Mg |
| | 24 | 0.7 | 0.6 | T | 0.7 | 0.3 | R | 0.7 | 0.8 | Gr | 0.7 | 0.3 | R | 0.7 | 0.6 | Mg |
| | >40 | 0.8 | 2.3 | T | 0.8 | 1.7 | R | 1 | 2.3 | Gr | 0.8 | 1 | R | 0.7 | 3 | Mg |
| *Streptococcus agalactiae* (0008200) | 18 | 0.7 | 0.3 | T | 0.7 | 0.1 | R | 0.7 | 0.5 | Gr | 0.5 | 0.1 | R | 0.5 | 0.5 | Mg |
| | 24 | 0.7 | 0.6 | T | 0.7 | 0.3 | R | 0.7 | 0.8 | Gr | 0.5 | 0.3 | R | 0.5 | 0.8 | Mg |
| | >40 | 0.8 | 2.3 | T | 0.7 | 1.7 | R | 0.7 | 2 | Gr | 0.5 | 0.5 | R | 0.5 | 3 | Mg |
| *Streptococcus agalactiae* (0008206) | 18 | 0.7 | 0.3 | T | 0.7 | 0.3 | R | 0.7 | 0.6 | Gr | 0.7 | 0.1 | R | 0.7 | 0.6 | Mg |
| | 24 | 0.7 | 1 | T | 0.8 | 0.5 | R | 0.7 | 1 | Gr | 0.8 | 0.3 | R | 0.7 | 0.8 | Mg |
| | >40 | 0.8 | 2 | T | 1.2 | 2 | R | 0.8 | 2 | Gr | 1.2 | 0.8 | R | 0.7 | 3 | Mg |
| *Streptococcus agalactiae* (0101060) | 18 | 0.4 | 2.7 | T | 0.4 | 0.5 | R | 0.3 | 0.8 | Gr | 0.5 | 0.3 | R | 0.4 | 2.7 | Mg |
| | 24 | 0.5 | 3 | T | 0.5 | 0.8 | R | 0.4 | 1.7 | Gr | 0.7 | 0.6 | R | 0.4 | 2.7 | Mg |
| | >40 | 0.7 | 4 | T | 0.7 | 3 | R | 0.5 | 3.5 | Gr | 0.8 | 2.3 | R | 0.5 | 4 | Mg |

EXAMPLE 2

Modification of the Concentration of α-glucosidase Enzymatic Substrate

The above protocol was repeated, with the exception that the concentration of enzymatic substrate was varied.

Table 2 below gives the number of strains detected (considered to be positive when I≧0.6) as a function of the concentration of substrate.

TABLE 2

| Substrate | Incubation time | 100 mg/l | 200 mg/l | 300 mg/l |
|---|---|---|---|---|
| Magenta-α-Glu | 24 h | 2/8 | 7/8 | 7/8 |
|  | 48 h | 8/8 | 8/8 | 8/8 |
| RedA-α-Glu | 24 h | 1/8 | 5/8 | 6/8 |
|  | 48 h | 7/8 | 8/8 | 8/8 |
| Rose-α-Glu | 24 h | 1/8 | 3/8 | 6/8 |
|  | 48 h | 7/8 | 8/8 | 8/8 |
| X-α-Glu | 24 h | 3/8 | 7/8 | 7/8 |
|  | 48 h | 7/8 | 7/8 | 7/8 |
| GreenA-α-Glu | 24 h | 6/8 | 7/8 | 7/8 |
|  | 48 h | 8/8 | 8/8 | 7/8 |

This table demonstrates that the concentration of 200 or 300 mg/l gives good detection.

EXAMPLE 3

Use of an α-glucosidase Substrate and of a Substrate for a Different Enzymatic Activity The protocol described in example 1 was repeated with GreenA-α-Glu, except that 133 mg/l of this substrate were used, and that 0.047 g/l of aztreonam (ICN), 0.004 g/l of amphotericin B (Squibb) and the following components were added to the medium, after autoclaving:

medium 1: control medium corresponding to the medium of example 1 with GreenA-α-Glu, modified as indicated above, medium 2: 400 mg/l of 6-chloro-3-indolyl-β-D-cellobioside (Rose-β-cellobioside), medium 3: 400 mg/l of 6-chloro-3-indolyl-β-N-acetylglucosaminide (Rose-β-NAGlu) and 0.5 g/l of N-acetylglucosaminide.

The results are given in table 3 below, in which G, Co and T are as defined above, with, in the case of the Co column, Gr=green, G=gray, Mv=mauve, Mg=magenta, B=blue, Vi=violet and R=pink.

The strains are all derived from the applicant's collection.

TABLE 3

|  |  | Medium 1 | | Medium 2 | | Medium 3 | |
|---|---|---|---|---|---|---|---|
| Strains (accession No.) | T | G | Co | G | Co | G | Co |
| Streptococcus agalactiae | 18 | 0.2 | Gr | 0.2 | Gr | 0.3 | Gr |
| (0101060) | 24 | 0.2 | Gr | 0.2 | Gr | 0.4 | Gr |
|  | 48 | 0.2 | Gr | 0.2 | Gr | 0.4 | Gr |
| Streptococcus anginosus | 18 | 0.1 |  | 0.1 |  | 0.1 |  |
| (8507046) | 24 | 0.1 |  | 0.1 |  | 0.2 |  |
|  | 48 | 0.2 |  | 0.2 |  | 0.3 |  |
| Streptococcus pyogenes | 18 |  |  |  |  |  |  |
| (9805062) | 24 |  |  |  |  |  |  |
|  | 48 |  |  |  |  |  |  |
| Enterobacter cloacae | 18 | 2 |  | 2 | R |  |  |
| (0010003) | 24 | 2 | G | 2 | R |  |  |
|  | 48 | 3 | Gr | 3 | R |  |  |
| Enterococcus faecium | 18 | 0.2 |  | 0.2 | R | 0.4 | R |
| (0002043) | 24 | 0.3 |  | 0.2 | R | 0.5 | R |
|  | 48 | 0.3 |  | 0.3 | R | 0.5 | R |
| Enterococcus faecalis | 18 | 1 | Gr | 0.8 | Vi B | 0.7 | Vi |
| (9001117) | 24 | 1.3 | Gr | 1.3 | Vi B | 0.7 | Vi |
|  | 48 | 1.7 | Gr | 1.7 | B | 0.7 | Vi |
| Listeria monocytogenes | 18 | 0.1 |  | 0.1 |  |  |  |
| (8309007) | 24 | 0.2 | Gr | 0.2 | Gr G | 0.1 |  |
|  | 48 | 0.3 | Gr | 0.2 | G Vi | 0.4 |  |
| Candida albicans | 18 |  |  |  |  |  |  |
| (9306081) | 24 |  |  |  |  |  |  |
|  | 48 |  |  |  |  |  |  |

This table demonstrates the fact that the use of a second enzymatic substrate makes it possible to improve the specificity of the detection without, however, degrading the sensitivity of detection of Streptococci B, and that it is possible to distinguish Streptococci B from the closest species most commonly encountered in an associated manner, after incubation for 24 h.

EXAMPLE 4

Comparison of the Sensitivity of Detection of S. agalactiae using a Medium Containing an α-glucosidase Substrate According to the Invention and the Commercially Available Media For this sensitivity study, a medium according to the invention, prepared as described in the above examples, but containing 0.130 g/l of GreenA-α-Glu, 0.250 g/l of Rose-β-D-cellobioside, 0.064 g/l of aztreonam and 0.004 g/l of amphotericin B (α-Glu medium), was used.

As medium for comparison, the Granada medium (ref 10 077, BIOLYS, France) (Granada medium) was used.

69 strains of microorganisms, including 14 of *Streptococcus agalactiae,* were inoculated and left to incubate at 37° C. for up to 24 h and at ambient temperature beyond this time. The colonies were visualized as described above. The confirmation of the colonies suspected of being characteristic of *Streptococcus* B, i.e. colonies that appeared to be green in color, was carried out by means of an agglutination assay using the SLIDEX Strepto Kit reagent according to the supplier's recommendations (bioMérieux, France). The non-characteristic colonies, i.e. those that were other than green or that had the characteristic coloration but gave a negative response in the agglutination assay (false-positive strains), were identified by means of Galerie ID 32 Strep (bioMérieux, France).

The results are expressed as % of correct diagnosis relative to all the tests in terms of sensitivity and specificity, and are given in table 4 below, the % sensitivity corresponding to the number of true positives detected on the medium divided by the total number of true positives to be detected (*100) and the % specificity corresponding to the number of true negatives detected on the medium divided by the total number of true negatives to be detected (*100).

TABLE 4

| | % sensitivity and specificity of detection of *S. agalactiae* | | | | | |
|---|---|---|---|---|---|---|
| | Granada medium | | | Alpha-Glu medium | | |
| | 18 h | 24 h | >40 h | 18 h | 24 h | >40 h |
| Sensitivity | 50 | 50 | 50 | 86 | 79 | 93 |
| Specificity without enrichment | 100 | 100 | 100 | 100 | 95 | 95 |
| Specificity with enrichment | 100 | 100 | 100 | 100 | 100 | 98 |

The results indicated in this table demonstrate the improvement in the sensitivity of detection of Streptococci B using the method of the invention. Moreover, they also show that the detection medium of the invention also has good specificity, which specificity is improved after enrichment due to a passage in Todd-Hewitt broth for 18-24 hours at 35-37° C. with or without 5% $CO_2$ before inoculation of the agar (see CDC (Center for Disease Control) recommendations, MMWR (Morbidity and Mortality Weekly Report), Aug. 16, 2002, vol. 51, No. RR-11).

EXAMPLE 5

Use of the Medium Based on Clinical Samples

For this study, the medium according to the invention, as prepared as described above in example 4, was used.

A total of 134 samples/swabs originating from vaginal or endocervical specimens from pregnant women were used in this study.

Each swab was emulsified in 1 ml of sterile physiological saline and 100 µl of this solution were deposited, firstly, onto a Columbia agar containing 5% of horse blood and, secondly, onto the medium using the method of the invention. Moreover, 100 µl of the above solution were used to inoculate a Todd-Hewitt broth. After incubation for 20 hours at 37° C. and under aerobic conditions, the blood-agar and the medium of the invention were inoculated using the Todd-Hewitt broth, and then incubated at 37° C. for 20 h under aerobic conditions.

The confirmation of the colonies suspected of being characteristic of *Streptococcus* B, i.e. that appeared green in color, was carried out by means of an agglutination assay using the SLIDEX Strepto Kit reagent according to the supplier's recommendations (bioMérieux, France).

Among the 134 samples, 112 were inoculated onto the agar media, firstly directly from the suspension in physiological saline and, secondly, after enrichment in Todd-Hewitt broth. The remaining 22 samples were inoculated onto the agar media only directly from the suspension in physiological saline.

The results, calculated as average percentage sensitivity and specificity, are presented in table 5 below.

TABLE 5

| | Columbia agar | Invention agar |
|---|---|---|
| Sensitivity | 95 | 90 |
| Specificity | 90 | 96 |

The results in the table show that the medium, used with clinical samples, has good sensitivity (18/20 *Streptococcus agalactiae* detected) and that the specificity of detection is improved compared with a standard medium (10 false + results against 24 on the Columbia blood medium), these results being substantially equivalent to those obtained using the laboratory strains.

What is claimed is:

1. A method for determining whether *Streptococcus agalactiae* are present in a sample, the method comprising:
   a) inoculating a reaction medium with the sample, the reaction medium formulated for the specific detection of *S. agalactiae* comprising at least one chromogenic or fluorescent α-glucosidase enzymatic substrate;
   b) incubating the inoculated reaction medium; and
   c) detecting a presence of a colored or fluorescent product; wherein the presence of a colored or fluorescent product indicates the presence of *Streptococcus agalactiae* in the sample.

2. The method as claimed in claim 1, wherein the enzymatic substrate is an indoxyl-derivative-based substrate.

3. The method as claimed in claim 2, wherein the concentration of the enzymatic substrate in the reaction medium is between 10 and 2000 mg/l.

4. The method as claimed in claim 1, wherein said reaction medium also comprises a mixture of aztreonam and amphotericin B.

5. The method as claimed in claim 1, wherein the reaction medium also comprises a substrate for detecting an enzymatic activity different from α-glucosidase activity.

6. The method as claimed in claim 5, wherein the substrate having an enzymatic activity different from α-glucosidase activity is selected from the group consisting of β-cellobiosidase substrates and β-glucosaminidase substrates.

7. The method as claimed in claim 1, wherein the reaction medium further comprises antibiotics.

8. The method as claimed in claim 1, wherein the α-glucosidase enzymatic substrate is at least one substrate selected from the group consisting of 6-bromo-3-indolyl-α-D-glucopyranoside, 6-chloro-3-indolyl-α-D-glucopyranoside, 5-bromo-6-chloro-3-indolyl-α-D-glucopyranoside, 5-bromo-4-chloro-3-indolyl-α-D-glucopyranoside, and 5-bromo-4-chloro-3-indolyl-N-methyl-α-D-glucopyranoside.

9. The method as claimed in claim 8, wherein two or more α-glucosidase enzymatic substrates are selected.

* * * * *